United States Patent
Ikuta et al.

(10) Patent No.: US 11,254,910 B2
(45) Date of Patent: Feb. 22, 2022

(54) METHOD FOR PRODUCING DIFFERENT POPULATIONS OF MOLECULES OR FINE PARTICLES WITH ARBITRARY DISTRIBUTION FORMS AND DISTRIBUTION DENSITIES SIMULTANEOUSLY AND IN QUANTITY, AND MASKING

(71) Applicant: Japan Science and Technology Agency, Saitama (JP)

(72) Inventors: Koji Ikuta, Aichi (JP); Masashi Ikeuchi, Aichi (JP)

(73) Assignee: JAPAN SCIENCE AND TECHNOLOGY AGENCY, Saitama (JP)

( * ) Notice: Subject to any disclaimer, the term of this patent is extended or adjusted under 35 U.S.C. 154(b) by 595 days.

(21) Appl. No.: 14/461,939

(22) Filed: Aug. 18, 2014

(65) Prior Publication Data
US 2014/0356954 A1    Dec. 4, 2014

Related U.S. Application Data

(63) Continuation of application No. 12/998,095, filed as application No. PCT/JP2009/064899 on Aug. 20, 2009, now Pat. No. 8,808,787.

(30) Foreign Application Priority Data

Sep. 17, 2008    (JP) .............................. JP2008-237696

(51) Int. Cl.
*C12N 5/00*      (2006.01)
*C12N 11/04*     (2006.01)
(Continued)

(52) U.S. Cl.
CPC .......... *C12N 5/0068* (2013.01); *B05C 21/005* (2013.01); *B05D 1/32* (2013.01);
(Continued)

(58) Field of Classification Search
CPC ............... B05D 1/32; B49D 1/52; G01N 1/28
(Continued)

(56) References Cited

U.S. PATENT DOCUMENTS

| 3,936,531 | A | * | 2/1976 | Hofer | ....................... B05D 1/32 427/154 |
|---|---|---|---|---|---|
| 5,895,692 | A | | 4/1999 | Shirasaki et al. | |
| 2005/0136668 | A1 | | 6/2005 | Yotsuya | |

FOREIGN PATENT DOCUMENTS

| JP | 355124573 A | * | 9/1980 | ............... B05D 1/32 |
|---|---|---|---|---|
| JP | 2003-517581 A | | 5/2003 | |

(Continued)

OTHER PUBLICATIONS

Ikeuchi et al.; "Divelopment of cell patterning device for cluster culture of stem cells"; School of Enginerring, Nagoya University, Japan et al.; J JSCAS vol. 10, No. 3, 3 pages,; 2008.
(Continued)

*Primary Examiner* — Dah-Wei D. Yuan
*Assistant Examiner* — Andrew J Bowman
(74) *Attorney, Agent, or Firm* — Michael Best & Friedrich LLP

(57) ABSTRACT

A masking member contains parallel through-holes, each of the through-holes contains a tilted wall structure; an upper end of the tilted wall structure of one of the through-holes abuts on an upper end of the tilted wall structure of an adjacent one of the through-holes thereby forming a knife-edge ridge at the upper ends. The masking member may in contact with a substrate. Formation in quantity of various different populations of a substance being studied with
(Continued)

multiple combinations of distribution form and distribution density may be conducted by dripping a suspension of a single concentration of the substance onto the masking member.

3 Claims, 7 Drawing Sheets

(51) Int. Cl.
    *B05C 21/00*      (2006.01)
    *B05D 1/32*      (2006.01)
    *C12N 5/071*      (2010.01)
    *C23C 30/00*      (2006.01)
    *H01L 21/02*      (2006.01)

(52) U.S. Cl.
    CPC ............ *C12N 5/0677* (2013.01); *C12N 11/04* (2013.01); *C23C 30/00* (2013.01); *H01L 21/02494* (2013.01); *H01L 21/02587* (2013.01); *H01L 21/02628* (2013.01); *C12N 2535/10* (2013.01)

(58) Field of Classification Search
    USPC .......................................... 427/49, 154, 226
    See application file for complete search history.

(56) References Cited

FOREIGN PATENT DOCUMENTS

| WO | WO 00/49382 | * | 8/2000 | ............... G01N 1/28 |
|---|---|---|---|---|
| WO | WO-2007/087402 A2 | | 8/2007 | |
| WO | WO-2007/148733 A1 | | 12/2007 | |

OTHER PUBLICATIONS

International Search Report issued in Application No. PCT/JP2009/064899, dated Jun. 10, 2009.

* cited by examiner

METHOD FOR PRODUCING DIFFERENT POPULATIONS OF MOLECULES OR FINE PARTICLES WITH ARBITRARY DISTRIBUTION FORMS AND DISTRIBUTION DENSITIES SIMULTANEOUSLY AND IN QUANTITY, AND MASKING

This application is a continuation of U.S. patent application Ser. No. 12/998,095 filed on May 31, 2011 which is an application filed under 35 U.S.C. § 371 based on PCT/JP2009/064899 filed on Aug. 20, 2009, the contents of which, including the specification, the claims and the drawings, are incorporated herein by reference in their entirety.

FIELD OF THE INVENTION

The present invention relates to a method for forming populations of molecules or fine particles on a substrate by specifying distribution forms and distribution densities. Specifically, the present invention relates to a method for forming in quantity various different populations of a substance being studied with multiple combinations of distribution form and distribution density from a solution or a suspension of said substance on the same substrate and in a single operation, making use of sedimentation of substances, and the devices to implement said method (hereafter called masking members).

BACKGROUND ART

A process for forming populations of fine particles or molecules on a substrate with specified distribution forms and distribution densities is increasingly important in many fields.

In tissue engineering research, for instance, cells are cultured and aggregated three-dimensionally to study the functions of cells in vitro. According to a known technique, cells are cultured in a floating condition in a vessel the surface of which is specially treated to prevent cell adhesion. The cells are then self-aggregated to form small globules through the action of the oscillation of fluids and the adhesive force of the cells. In another method, cells are cultured and self-organized in a gel where they can move freely. With these techniques, aggregation takes place randomly and the size of the formed aggregates varies widely from tens to several hundreds of micrometers even though the same vessel is used.

Techniques to achieve cell aggregation to a desired size include (1) using a small cylindrical vessel and (2) using a substrate with a number of small through-holes. In these methods, a suspension is added to such a substrate with micro-holes on its flat surface. The cells settle out on the substrate in the form defined by the hole configuration, eventually enabling researchers to achieve a result with the desired cell aggregates.

The process of forming populations of fine particles or molecules with a specified distribution form and distribution density is also very important when adding gene transfer agents or other biochemical reagents locally into cells being cultured with a specified concentration that induces cell differentiation. In the electronics industry, technologies to deposit metal nanoparticles and other functional materials on substrates with specified patterns are actively being studied as a new printed circuit board fabrication process.

Examples of patent publications related to the above technologies include:

Patent literature 1: Patent Application Publication No. 2006-055069
Patent literature 2: Patent Application Publication No. 2006-122012

DESCRIPTION OF THE INVENTION

Tasks to be Solved by the Present Invention

The optimum distribution form and distribution density of aggregates differ depending on the substance or its functions to be studied. It is therefore necessary to experimentally determine the optimum form and density by producing populations of the substance with various combinations of forms and density. With the conventional methods, it is theoretically possible to derive aggregates with various forms collectively on a single substrate by using various arrangements of holes in multiple forms.

For distribution density, however, multiple substrates must be prepared, and on each substrate a solution or suspension of the substance in a different concentration is placed to produce the required aggregates. With conventional methods, furthermore, the areas between adjacent holes are flat, which allows the substance to settle. Substance settling on the flat surfaces does not participate in forming aggregates, and thus the efficient use of the substance is degraded.

Another shortcoming of conventional methods is that the substance settling on small vessels or areas other than the holes in the initial stage of settling will gradually enter the holes due to oscillation of the surrounding liquids and this action will disturb the stable formation of aggregates.

One of the tasks of the present invention is to provide a method for forming in quantity various different populations of a substance being studied with multiple combinations of distribution form and distribution density on the same substrate by dripping a solution or suspension of said substance in a single concentration on a masking member of a certain specified structure that is placed on the substrate, thereby making use of the sedimentation of the substance, and the masking members to implement said task.

Another task of the present invention is to provide a method to improve the efficiency of the use of substances by reducing the rate of substances that are deposited on areas outside the target area and thus do not participate in forming populations, and the masking members to implement said task.

Another task of the present invention is to provide a method to prevent the substance deposited on areas outside the target area in the initial stage of settling from entering the target area due to oscillation of fluids or similar cause in the later stage of settling, and the masking members to implement said task.

According to the present invention, the above tasks are solved by the method for forming in quantity various different populations of a substance being studied with multiple combinations of distribution form and distribution density from a solution or a suspension of said substance that are formed on a substrate; wherein said method comprises a process for fabricating masking members with a tilted wall structure specifically designed to achieve the target distribution form and distribution density and a process for adding a solution or suspension of the substance to said masking members placed on the substrate and allowing the substance to settle on the substrate in the region defined by said tilted wall structure, and thereby said method enables the substance that passes through the region bounded by the upper boundary of the wall structure to settle on the substrate in the specified region bounded by the lower boundary of the wall structure.

Means to Solve the Problems

To solve the problems mentioned above, the present invention provides:

A technical means to form populations of fine particles or molecules on a substrate by specifying the distribution form and distribution surface density. Specifically, a method for producing various different populations of molecules or particles with arbitrary distribution forms and distribution densities simultaneously and in quantity, wherein a masking member that is provided with parallel through-holes and having a tilted wall structure to achieve the target distribution form and distribution density is prepared; a solution or a suspension of the substance being studied is dripped onto said masking member which is positioned in close contact with a substrate; and said substance settles through the region defined by the tilted wall structure of the masking member, with the result that the substance settling along the tilted wall structure and passing through the region bounded by the upper boundary of said wall structure deposits onto the substrate in the area bounded by the lower boundary of the wall structure;

The above method for producing various different populations of molecules or particles with arbitrary distribution forms and distribution densities simultaneously and in quantity, wherein said fine particles or molecules may be cells, proteins, nucleic acids, bio-derived polymers, metal nanoparticles, semiconductor particles, or resin particles;

The above method for producing various different populations of molecules or particles with arbitrary distribution forms and distribution densities simultaneously and in quantity, wherein the liquids in which the substance being studied is dissolved or suspended are those that do not react with the masking members;

The above method for producing various different populations of molecules or particles with arbitrary distribution forms and distribution densities simultaneously and in quantity, wherein said wall structure is provided with grooves on its surfaces parallel to the upper boundary of the wall structure of said masking member;

The above method for producing various different populations of molecules or particles with arbitrary distribution forms and distribution densities simultaneously and in quantity, wherein all surfaces of said masking member are either provided with grooves or tilted toward the lower opening, or provided with without any horizontal surfaces on said masking member;

The above method for producing various different populations of molecules or particles with arbitrary distribution forms and distribution densities simultaneously and in quantity, wherein the surfaces of the wall structure of said masking member are made of materials that resist the adhesion of the substance being studied;

The above method for producing various different populations of molecules or particles with arbitrary distribution forms and distribution densities simultaneously and in quantity, wherein all or part of the substrate on which said masking member is placed uses porous materials, fibrous materials, or gels or a combination of any of these;

A masking member used in said method for forming populations of molecules or fine particles on a substrate in specified distribution forms and distribution densities, wherein the form of the upper opening and lower opening is defined arbitrarily and independently, and both openings are connected by a tilted wall structure;

The above masking member wherein grooves are formed on the surfaces of the wall structure parallel to the upper boundary line of the wall structure of said masking member;

The above masking member wherein all of its surfaces are provided with grooves or tilted toward the lower opening, and there are no horizontal surfaces on said masking member;

The above masking member wherein the surfaces of its wall structure are made of materials that resist adhesion of the substance being studied;

The above masking member wherein the structural material of said masking member is silicon rubber or fluorine rubber or a combination of these materials;

The above masking member wherein the surface modifying material used for its wall structure is polyethylene glycol, polypropylene glycol, polyvinyl alcohol, polyacrylic acid, polymethacrylic acid, polyacrylic amide, or any hydrophilic polymers comprising a combination of any of these substances.

Effects of the Invention

According to the present invention, the following excellent effects are expected:

1) From a solution or a suspension containing a single concentration of a substance being studied, various different populations of the substance with arbitrary distribution forms and distribution densities are formed on the surface of various substrates made of different materials collectively, in quantity and in a single operation, enabling researchers to perform analyses efficiently with a variety of combinations of forms and densities.

2) According to the method of the present invention, almost all of the samples are effectively used and formed into populations for analysis, thereby reducing consumption of precious and rare materials.

LEGEND

1 Masking member
2 Upper boundary (upper opening)
3 Lower boundary (lower opening)
4 Tilted wall structure
5 Peripheral groove
6 Substrate
7 Wall

BEST MODE FOR CARRYING OUT THE INVENTION

The method according to the present invention comprises a process for fabricating masking members with a tilted wall structure specifically designed to achieve a target distribution form and distribution density, and a process for adding a solution or suspension of a substance being studied to said masking members that are placed on a substrate and allowing the substance to settle in the region defined by said tilted wall structure, whereby said method enables the substance that passes through the region bounded by the upper boundary of the wall structure to settle on the substrate in the specified region bounded by the lower boundary of the wall structure.

Embodiments

Figure 1:
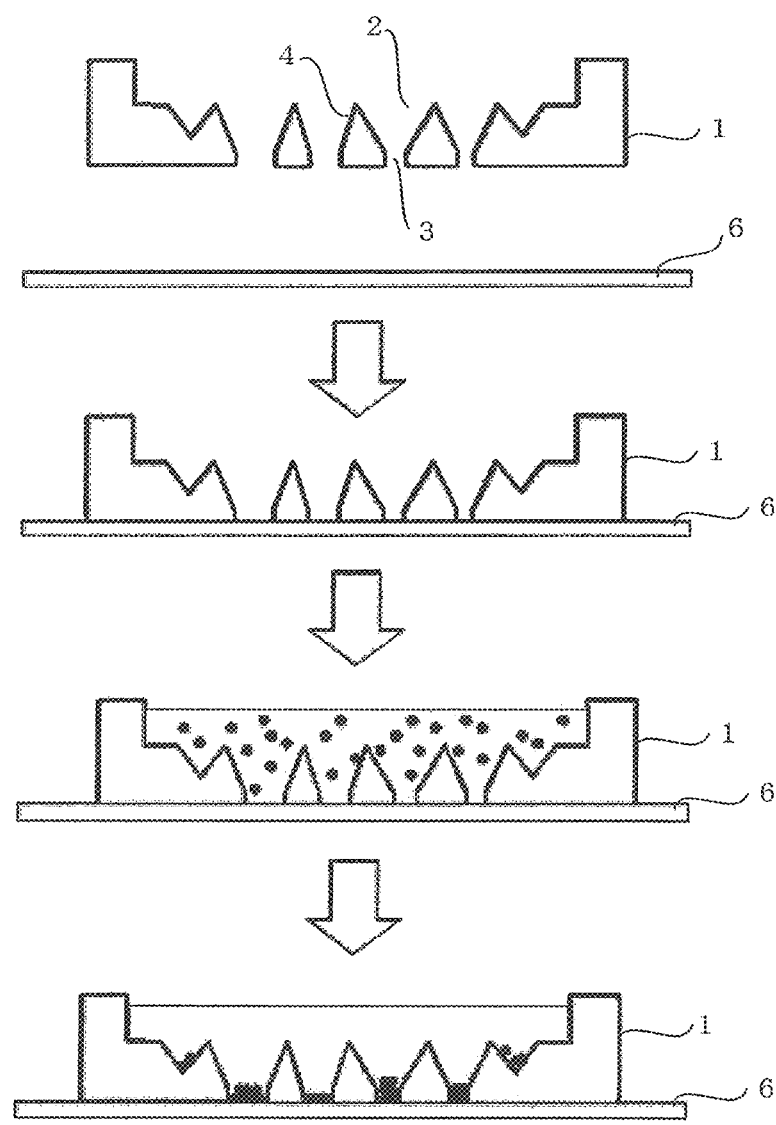
FIG. 1 is a cross-sectional schematic diagram showing a typical masking member with a tilted wall structure of the present invention and the substance population forming method using said masking member.
Figure 2:
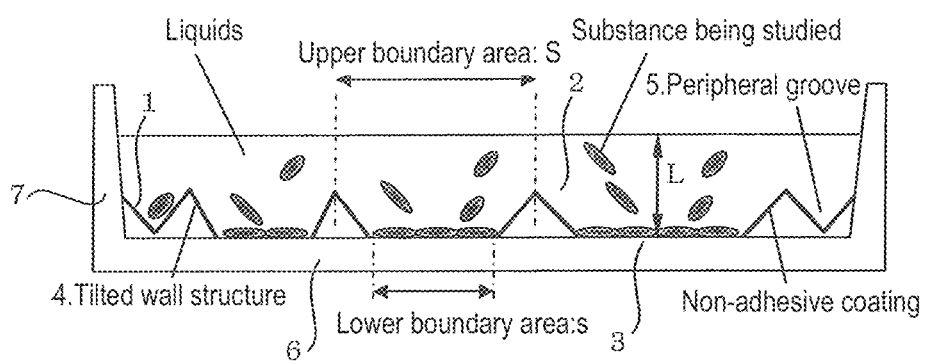
FIG. 2 is a cross-sectional schematic diagram showing an example of the masking member with a tilted wall structure and the substance population forming method using said masking member shown in FIG. 1.
Figure 3:
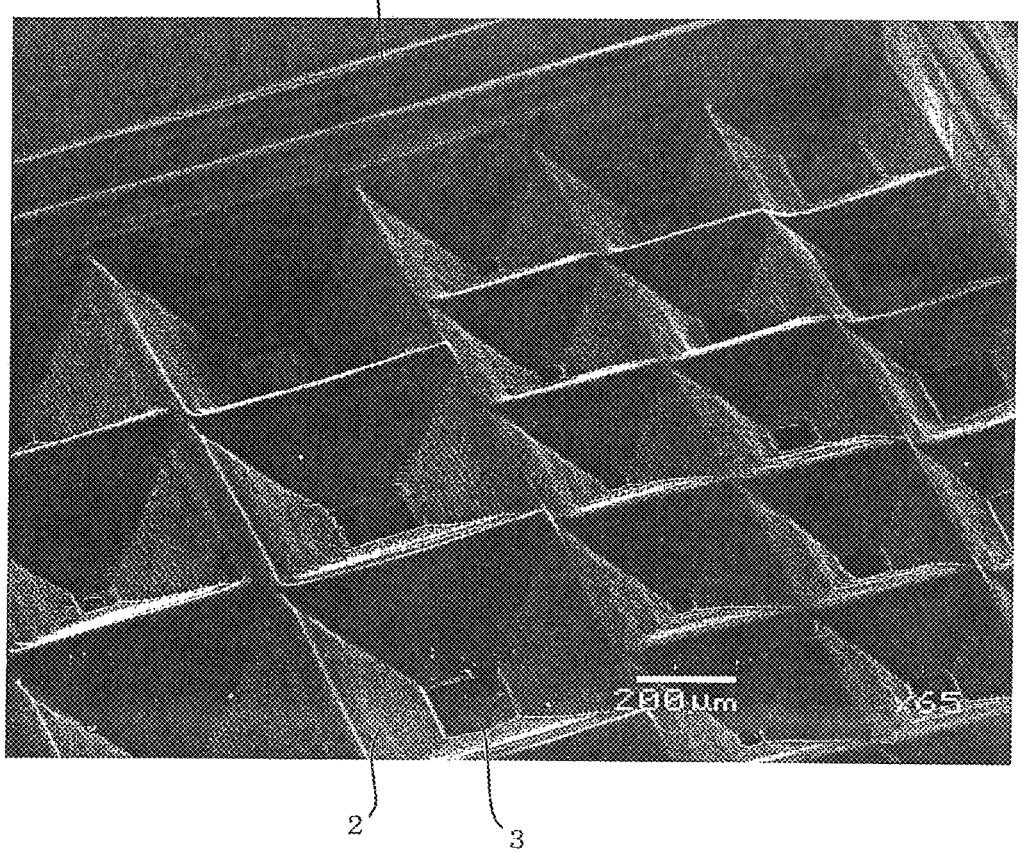
FIG. 3 is an electron micrograph of an embodiment of the masking member with the tilted wall structure viewed obliquely.
Figure 4:
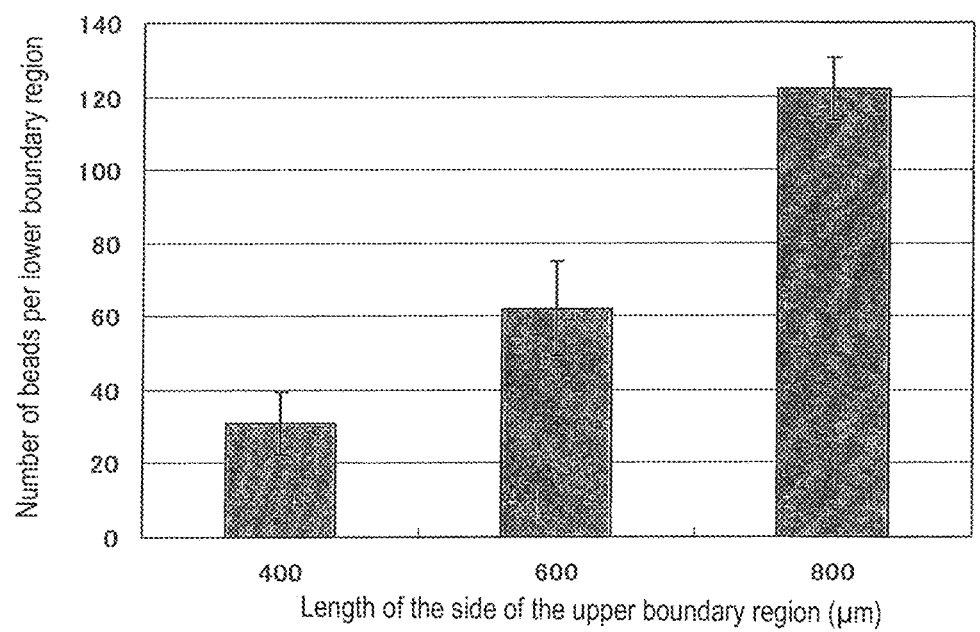
FIG. 4 is a graph showing the relationship between the length of a side of the upper boundary region and the number of beads deposited on the lower boundary region for the population of beads formed with the masking member shown in FIG. 2.
Figure 5:
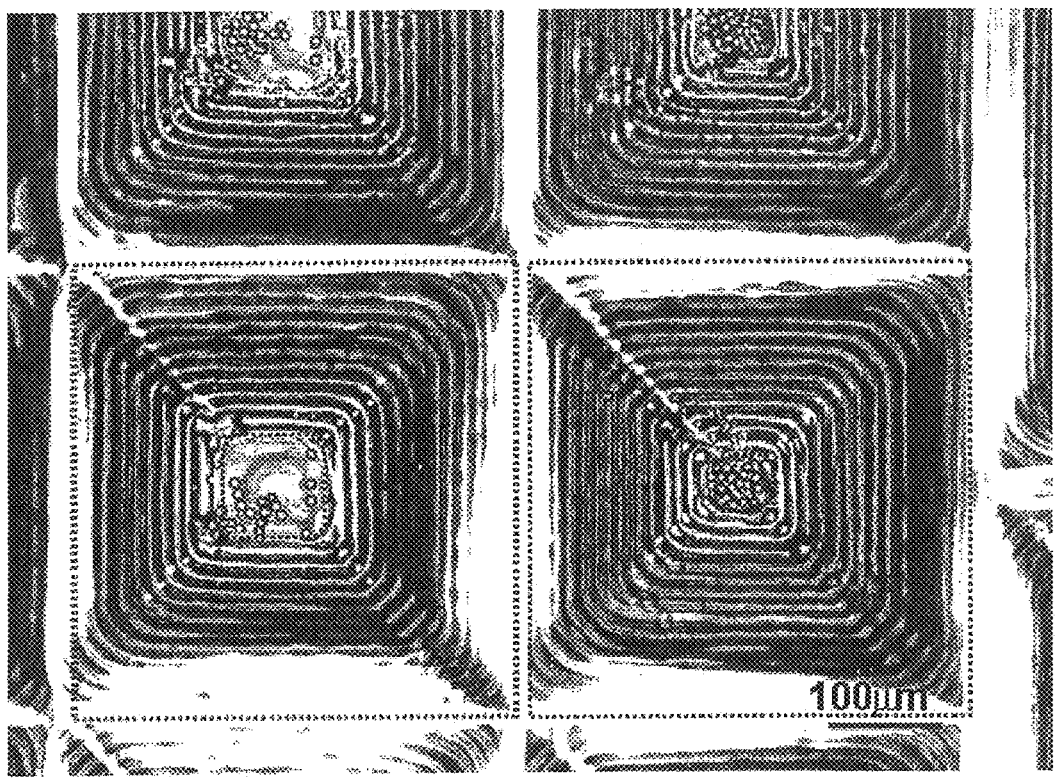
FIG. 5 is an optical micrograph of micro-beads formed into populations.

The embodiments of the present invention are explained with reference to the drawings. FIG. 1 is a cross-sectional schematic diagram showing a typical masking member with a tilted wall structure of the present invention and the substance population forming method using said masking member. FIG. 2 is a cross-sectional schematic diagram showing an example of the masking member with a tilted wall structure and the substance population forming method using said masking member similar to the masking member shown in FIG. 1. FIG. 3 is an electron micrograph of an embodiment of the masking member with the tilted wall structure viewed obliquely. FIG. 4 is a graph showing the relationship between the length of a side of the upper boundary region and the number of beads deposited on the lower boundary region for the population of beads formed with the masking member shown in FIG. 3. FIG. 5 is an optical micrograph of micro-beads formed into populations.

In FIGS. 1 and 2, 1 is the masking member. The masking member defines the form of the upper opening (upper boundary) 2 and that of the lower opening (lower boundary) 3 arbitrarily and independently. These two openings are connected by the tilted wall structure (tilted wall surface) 4 to form a concave space resembling an inverted pyramid. The masking member is provided with a number of these concave spaces arranged in a grid as shown in FIG. 3. The shape of the concave space is not limited to the inverted pyramid shape but may be an inverted cone or an inverted triangular pyramid. The tilted wall structure may have different tilt angles in multiple steps as and when necessary.

A peripheral groove 5 is formed, as appropriate, on the periphery of the masking member 1 as shown in FIG. 2. The boundary between two adjacent concave spaces is in the form of a knife-edge ridge where the two adjacent surfaces abut each other. By designing tilted surfaces for the entire wall structure, it is possible to prevent the substance being studied from depositing on any areas other than the target area. By forming a peripheral groove on the periphery of the masking member, it is possible to prevent intrusion of a non-uniform substance due to the effects of the sides of a vessel.

The substrate 6 on which said masking member 1 is located has a wall 7 in FIG. 2. In this embodiment, the masking member 1 is positioned inside said wall 7 as shown in FIG. 2. The wall 7 formed around the substrate 6 is not essential and may be omitted as appropriate.

As stated above and according to the present invention, the distribution form of the substance being studied can be defined by the lower boundary (the form of the lower opening) of the wall structure. Assuming the area of the region bounded by the lower boundary of the wall structure (the area of the lower opening) is s (mm2), the area of the region bounded by the upper boundary of the wall structure (the area of the upper opening) S (mm2), the concentration of the solution or suspension of the substance being studied C (mm-3), and the depth of the liquids to be added L (mm), then the distribution surface density D (mm-2) of the substance deposited on the specified region bounded by the lower boundary of the wall structure is given by the following equation:

$$D = CLS/s$$

It is therefore possible to form populations of substances with arbitrary distribution forms and distribution densities on a substrate by specifying the upper boundary and lower boundary of the tilted wall structure independently. Furthermore, by prefabricating a masking member provided with a number of multiple combinations of the form of the upper and lower boundary, and using a solution or a suspension containing a single concentration of the substance being studied, it is possible to collectively form various different populations of the substance with arbitrary distribution forms and distribution densities on a single substrate, which is placed under said masking member, with a single operation of dripping said solution or suspension onto said masking member.

In the present invention described above, when all of the surfaces of the tilted wall structures of the masking member 1 are tilted toward the lower boundary, the deposition of substances on any area other than the target area is prevented, and almost all of the samples are effectively used and formed into populations for analysis.

In the present invention described above, by providing grooves on the surfaces of the wall structure 4 of the masking member 1 parallel to the upper boundary line of the wall structure, any substance deposited on areas outside the target area in the initial stage of settling is prevented from entering the target area unintentionally in the later stage of settling.

The tilted wall structure section, upper surface, and bottom surface of the masking member 1 with the tilted wall structure of the present invention may be made of the same material or of respectively different materials.

The masking member with the tilted wall structure of the present invention is preferably surface-modified or coated with a substance that resists adhesion of the substance being studied at least in the tilted wall section, but this may not apply when the material of the masking member itself resists adhesion of the substance being studied.

The liquid in which the substance being studied is dissolved or suspended may be a liquid that does not react with the masking member.

The substance to be formed into populations using the method of the present invention may be cells, proteins, nucleic acids, bio-derived polymers, metal nanoparticles, semiconductor particles, ceramic particles, or resin particles, or any system representing a combination of any of the above.

Embodiment 1: Formation of Aggregates of Micro-Beads

One of the embodiments of the present invention is the formation of 10 μm diameter latex-made micro-beads into desired populations. A masking member with tilted wall structures in the form of an inverted pyramid is molded from PDMS materials as shown in FIG. 3. The molding die for the masking member was manufactured by stereolithography using epoxy photosensitive resins, but the fabrication method for said masking member of the present invention is not limited to this one.

The side of the square of the upper boundary region of the tilted wall structure is 400, 600 or 800 μm while that of the lower boundary region is 40, 80 or 160 μm. A number of tilted wall structures each having a total of 9 different combinations of upper and lower boundary regions were densely formed on a substrate measuring 8 mm square.

Said masking member was attached to a glass substrate, and a 50 μl micro-bead suspension of a s2.3×105 beads/ml concentration was dripped onto said masking members. It was confirmed that the number of beads deposited onto the substrate in the respective region bounded by the walls was proportional to the area of the corresponding upper boundary region, or nearly the same as the theoretical value (FIG. 4). It was also confirmed that the distribution surface density of the beads deposited on the lower boundary region was inversely proportional to the area of the lower boundary region (FIG. 5). There were no beads deposited any place outside the target region, or on other than the lower boundary region. This shows that by designing tilted surfaces for the entire wall structure, the substance being studied can be efficiently used for forming populations for analysis.

The above results show that, using the method of the present invention, it is possible to collectively form populations of micro-beads having the specified distribution form and distribution surface density on a single substrate using a suspension of a single concentration.

Embodiment 2: Formation of Cell Aggregates on a Non-Adhesive Plastic Substrate

Figure 6:
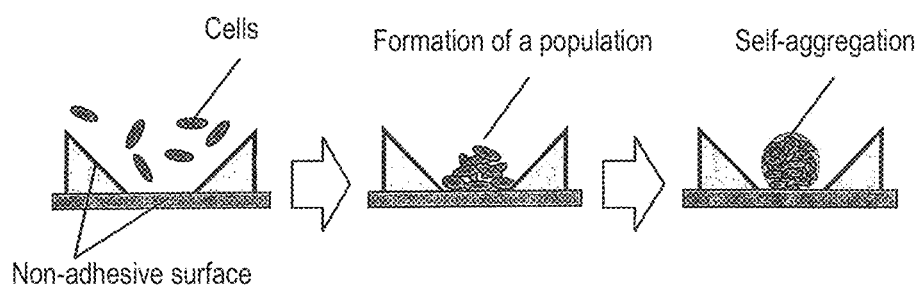
FIG. 6 is a diagram showing the formation of cell aggregates in a floating condition.

The schematic diagram of an application of the present invention shown in FIG. 6 is an example of the formation of cell aggregates in a floating condition. Cells deposit onto the substrate and assemble. Since the substrate is non-adhesive to the cells, the cells stick only to one another and grow spontaneously into a spherical cell aggregate.

When culturing cells in a floating condition, adjacent cells are known to join together spontaneously and form aggregates of about 200 μm at maximum. Using the method of the present invention, it is now possible to observe spontaneous formation of cell aggregates in a floating condition by specifying the initial number of cells and cell distribution density (FIG. 6). Mouse pancreatic stem cells were used in the embodiment described below.

A masking member of PDMS material with the shape shown in FIG. 3 was fabricated in the same way as in embodiment 1. The surface of the masking member was immersed in an amphiphilic polymer PEG solution to make the surface hydrophilic. This is an effective means for suppressing the cell adhesion on the surface of the masking member. The processed masking member was placed on a substrate that is non-adhesive to cells.

Figure 7:
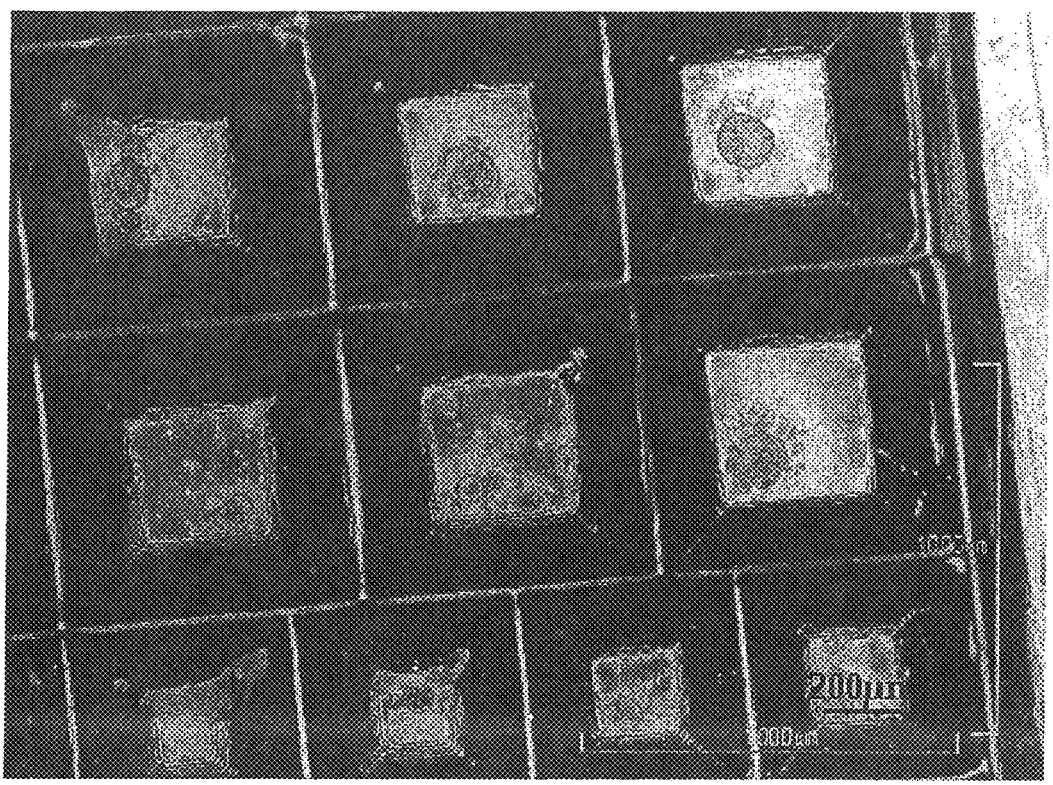
FIG. 7 is a photograph showing aggregates of pancreatic stem cells cultured from a 200 µl cell suspension of a 2×105 cells/ml concentration on the non-adhesive masking member for three days at 37° C. in a 5% $CO_2$ atmosphere.

FIG. 7 is a photograph showing aggregates of pancreatic stem cells cultured from a 200 μl cell suspension of a 2×105 cells/ml concentration on the non-adhesive masking member for three days at 37° C. in a 5% $CO_2$ atmosphere. Two days later, formation of spherical cell coagulations was confirmed in the regions bounded by the walls. The size of the coagulation was proportional to the area of the upper boundary region or the initial number of cells (FIG. 7). No significant effect of the initial distribution density was observed within the conditions set for this particular experiment.

The above results show that, using the method of the present invention, experiments on a number of combinations of distribution form (size) and distribution density of the substance being studied can be collectively performed successfully with just a single preparatory operation.

Embodiment 3: Formation of Cell Aggregates on Cell-Adhesive Plastic Substrate

Cells in living organisms are surrounded by polymers which are the base for adhesion. Outside a living organism, cells are cultured in polymer gels of high adhesiveness in an attempt to form a tissue that behaves similarly to that found in organisms. This is an important developmental theme in regenerative medicine.

Figure 8:
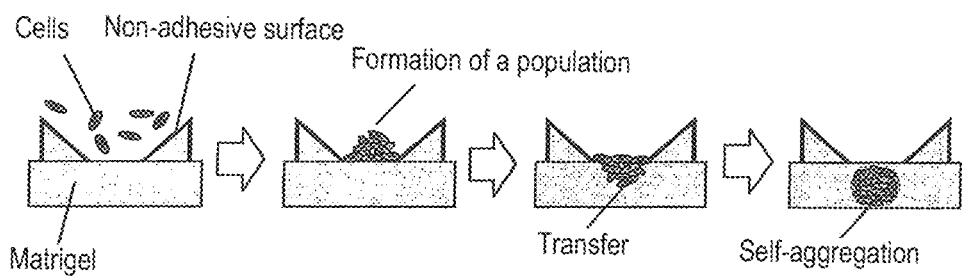
FIG. 8 is a cross-sectional schematic diagram to explain the formation of cell aggregates in the 3D matrix of the above embodiment.

FIG. 8 is the cross-sectional schematic diagram of a 3D gel matrix of the present embodiment. It is shown here to explain the formation of cell aggregates.

The cells deposit onto the lower opening of the masking member, and move spontaneously into the highly adhesive 3D gel matrix. For this reason, the cell populations that form on the surface of the substrate move into the gel over time. Once in the gel, the cells grow three-dimensionally to form a spherical aggregate spontaneously.

Using the method of the present invention, researchers can form cell populations with specified distribution forms and distribution surface densities on not only solid substrates but also on various other materials including gels that are most suitable for the cells to grow. In the embodiment described below, populations of mouse pancreatic stem cells were formed, using the masking member of the present invention, on the Matrigel layer, which is effective medium for cell growth, for the purpose of collectively studying the optimum initial conditions for developing a structure and function similar to those of the pancreatic islet of an organism (FIG. 8).

The masking member of PDMS material, having the shape shown in FIG. 3, was molded such that its bottom passes through and opens with its surfaces made hydrophilic using the method discussed in embodiment 2. The masking member was then placed on a 2 mm thick Matrigel layer and both parts were adhered to each other by the adsorption force of the gel.

Figure 9:
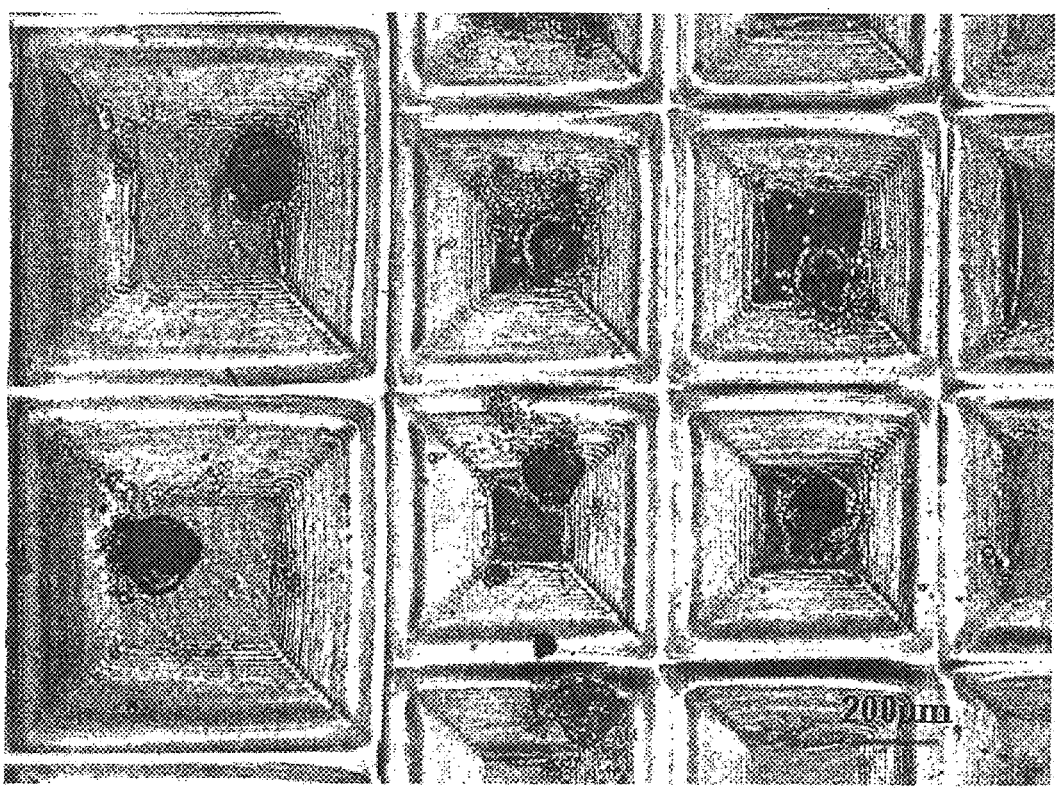
FIG. 9 is a photograph showing aggregates of pancreatic stem cells cultured for four days after populations are formed on Matrigel according to the present invention.

A 200 μl cell suspension of a 2×105 cells/ml concentration was dripped onto the above masking member and cultured at 37° C. in a 5% $CO_2$ atmosphere for four days. The cell populations formed on the surfaces of the Matrigel layers within the regions bounded by the walls and moved spontaneously into the Matrigel layer within a few hours. One day later, formation of the spherical cell coagulations was confirmed. The size of the coagulations was variable because the initial number of cells was determined to be proportional to the area of the upper boundary region (FIG. 9) as with the application example 2. The coagulations formed about 24 hours faster than the formation of coagulations in the floating condition in embodiment 2.

This occurred because there were many Matrigels, which are the base of movement and growth, around the cells. The above results show that, using the method of the present invention, it is possible to form populations of the substance being studied having the specified combination of distribution form (size) and distribution density on an arbitrary material.

The present invention has been explained herein citing some embodiments, but the present invention is not limited to these embodiments. For example, the materials of the masking member and the form of the concave space of the masking member can be freely selected to match the mother solution.

INDUSTRIAL APPLICABILITY

The present invention can be used in tissue engineering to reproduce the functions of cells in living organisms.

What is claimed is:

1. A masking member used for forming a population of molecules or particles on a substrate, the masking member comprising:
   concave spaces that extend into the masking member from an upper surface of the masking member and terminate at a lower surface;
   a wall that extends from the upper surface in a manner that surrounds the concave spaces; and
   a groove between the wall and one of the concave spaces,
   wherein a sidewall for the one of the concave spaces abuts a sidewall for an adjacent one of the concave spaces at the upper surface thereby forming a knife-edge ridge at the upper surface along a boundary between an opening for the one of the concave spaces and an opening for the adjacent one of the concave spaces,
   wherein the knife-edge ridge extends along a straight line in an oblique view of the masking member.

2. The masking member according to claim 1, wherein a shape of the opening for the one of the concave spaces and a shape of the opening for the adjacent one of the concave spaces are polygonal in the oblique view of the masking member.

3. The masking member according to claim 1, wherein the shape of the opening for the one of the concave spaces at the upper surface is a square in the oblique view of the masking member.

* * * * *